United States Patent
Roop et al.

(10) Patent No.: US 7,250,049 B2
(45) Date of Patent: Jul. 31, 2007

(54) ABLATION CATHETER WITH SUSPENSION SYSTEM INCORPORATING RIGID AND FLEXIBLE COMPONENTS

(75) Inventors: John Avi Roop, Crystal, MN (US); Kedar Ravindra Belhe, Minnetonka, MN (US); Hong Cao, Shakopee, MN (US); Saurav Paul, Minneapolis, MN (US)

(73) Assignee: St. Jude Medical, Atrial Fibrillation Division, Inc., Maple Grove, MN (US)

( * ) Notice: Subject to any disclaimer, the term of this patent is extended or adjusted under 35 U.S.C. 154(b) by 82 days.

(21) Appl. No.: 10/856,544

(22) Filed: May 27, 2004

(65) Prior Publication Data

US 2005/0267460 A1 Dec. 1, 2005

(51) Int. Cl. *A61B 18/14* (2006.01)
(52) U.S. Cl. .......................................................... 606/41
(58) Field of Classification Search ................. 606/41; 600/585
See application file for complete search history.

(56) References Cited

U.S. PATENT DOCUMENTS

| | | | |
|---|---|---|---|
| 3,924,632 A * | 12/1975 | Cook ........................ 604/527 |
| 4,641,656 A * | 2/1987 | Smits ........................... 607/5 |
| 5,268,316 A | 12/1993 | Robinson et al. | |
| 5,411,527 A * | 5/1995 | Alt ............................... 607/5 |
| 5,423,772 A * | 6/1995 | Lurie et al. ................. 604/525 |
| 5,445,148 A | 8/1995 | Jaraczewski et al. | |
| 5,464,404 A * | 11/1995 | Abela et al. .................. 606/15 |
| 5,487,757 A | 1/1996 | Truckai et al. | |
| 5,531,721 A * | 7/1996 | Pepin et al. ................. 604/525 |
| 5,545,193 A * | 8/1996 | Fleischman et al. .......... 607/99 |
| 5,549,581 A | 8/1996 | Lurie et al. | |
| 5,626,136 A * | 5/1997 | Webster, Jr. ................. 600/373 |
| 5,722,963 A | 3/1998 | Lurie et al. | |
| 5,779,669 A * | 7/1998 | Haissaguerre et al. ... 604/95.01 |
| 5,782,828 A | 7/1998 | Chen et al. | |
| 5,807,249 A | 9/1998 | Qin et al. | |
| 5,814,016 A * | 9/1998 | Valley et al. ............. 604/96.01 |
| 5,823,955 A | 10/1998 | Kuck et al. | |
| 5,843,020 A | 12/1998 | Tu et al. | |
| 5,871,523 A * | 2/1999 | Fleischman et al. .......... 607/99 |
| 5,882,346 A | 3/1999 | Pomeranz et al. | |
| 5,897,529 A | 4/1999 | Ponzi | |

(Continued)

OTHER PUBLICATIONS

Boston Scientific—Wiseguide Guide Catheter, http://www.bostonscientific.com, depicting the allRight™ Curve; CLS™ Curve; Q-Curve®; VODA Left® Curve; SmartShapes Guide Catheter; Zone Technology; and Wire Braid Pattern, (last visited on Jul. 13, 2004).

(Continued)

*Primary Examiner*—Michael Peffley
*Assistant Examiner*—Alex Toy
(74) *Attorney, Agent, or Firm*—Heimbecher & Assoc., LLC (57) ABSTRACT

A curved ablation catheter imparts ablative energy to target tissue, for example, along a trabecular slope, e.g., in the right atrium along the isthmus between the ostium of the inferior vena cava and the tricuspid valve. The catheter is formed with a preset curvature that, when deployed, both translates linearly and increases in radius to aid in the formation of spot or continuous linear lesions. A method of treating atrial flutter employs the curved ablation catheter.

17 Claims, 9 Drawing Sheets

U.S. PATENT DOCUMENTS

| | | | | |
|---|---|---|---|---|
| 5,916,214 A | * | 6/1999 | Cosio et al. | 606/41 |
| 5,931,811 A | | 8/1999 | Haissaguerre et al. | |
| 5,951,471 A | | 9/1999 | Rama et al. | |
| 5,993,462 A | | 11/1999 | Pomeranz et al. | |
| 6,001,085 A | | 12/1999 | Lurie et al. | |
| 6,002,955 A | | 12/1999 | Willems et al. | |
| 6,004,280 A | * | 12/1999 | Buck et al. | 600/585 |
| 6,013,076 A | * | 1/2000 | Goble et al. | 606/41 |
| 6,021,340 A | * | 2/2000 | Randolph et al. | 600/381 |
| 6,071,274 A | | 6/2000 | Thompson et al. | |
| 6,071,279 A | | 6/2000 | Whayne | |
| 6,080,151 A | | 6/2000 | Swartz et al. | |
| 6,083,216 A | * | 7/2000 | Fischer, Sr. | 604/530 |
| 6,090,104 A | * | 7/2000 | Webster, Jr. | 606/41 |
| 6,120,500 A | | 9/2000 | Bednaret et al. | |
| 6,219,582 B1 | * | 4/2001 | Hofstad et al. | 607/122 |
| 6,241,754 B1 | | 6/2001 | Swanson et al. | |
| 6,245,068 B1 | * | 6/2001 | Olson et al. | 606/41 |
| 6,264,654 B1 | | 7/2001 | Swartz et al. | |
| 6,308,091 B1 | | 10/2001 | Avitall | |
| 6,321,123 B1 | * | 11/2001 | Morris et al. | 607/122 |
| 6,580,949 B1 | * | 6/2003 | Tsuboi et al. | 607/125 |
| 6,605,087 B2 | | 8/2003 | Swartz et al. | |
| 6,622,731 B2 | * | 9/2003 | Daniel et al. | 128/898 |
| 2002/0173785 A1 | * | 11/2002 | Spear et al. | 606/41 |
| 2005/0228290 A1 | * | 10/2005 | Borovsky et al. | 600/466 |

OTHER PUBLICATIONS

Johnson & Johnson Gateway(SM), http://www.jnjgateway.com, "Vista Brite Tip" information, (last visited on Jul. 13, 2004).

Johnson & Johnson Gateway(SM), http://www.jnjgateway.com, Cordis "Vista Brite Tip Guiding Catheter" information, (last visited on Jul. 13, 2004).

Cordis Cardiology Product Catalog 2004, Vista Brite Tip Guiding Catheter, pp. D1-D6.

* cited by examiner

ABLATION CATHETER WITH SUSPENSION SYSTEM INCORPORATING RIGID AND FLEXIBLE COMPONENTS

BACKGROUND OF THE INVENTION a. Field of the Invention

The instant invention is directed toward an ablation catheter with a combination of rigid and flexible components for imparting ablative energy (e.g., radio frequency (RF) energy) to target tissue, for example, along a trabecular slope, e.g., in the right atrium along the isthmus between the ostium of the inferior vena cava and the tricuspid valve. The catheter acts as an armature suspension to aid in the formation of spot or continuous linear lesions on a trabecular surface.

b. Background Art

Catheters have been in use for medical procedures for many years. Catheters can be used for medical procedures to examine, diagnose, and treat while positioned at a specific location within the body that is otherwise inaccessible without more invasive procedures. During these procedures a catheter is inserted into a vessel located near the surface of a human body and is guided to a specific location within the body for examination, diagnosis, and treatment. For example, one procedure often referred to as "catheter ablation" utilizes a catheter to convey an electrical stimulus to a selected location within the human body to create tissue necrosis. Another procedure oftentimes referred to as "mapping" utilizes a catheter with sensing electrodes to monitor various forms of electrical activity in the human body.

In a normal heart, contraction and relaxation of the heart muscle (myocardium) takes place in an organized fashion as electrochemical signals pass sequentially through the myocardium from the sinoatrial (SA) node located in the right atrium to the atrialventricular (AV) node and then along a well defined route which includes the His-Purkinje system into the left and right ventricles. Sometimes abnormal rhythms occur in the atrium which are referred to as atrial arrhythmia. Three of the most common arrhythmia are ectopic atrial tachycardia, atrial fibrillation, and atrial flutter. Arrhythmia can result in significant patient discomfort and even death because of a number of associated problems, including the following: (1) an irregular heart rate, which causes a patient discomfort and anxiety; (2) loss of synchronous atrioventricular contractions which compromises cardiac hemodynamics resulting in varying levels of congestive heart failure; and (3) stasis of blood flow, which increases the vulnerability to thromboembolism. It is sometimes difficult to isolate a specific pathological cause for the arrhythmia although it is believed that the principal mechanism is one or a multitude of stray circuits within the left and/or right atrium. These circuits or stray electrical signals are believed to interfere with the normal electrochemical signals passing from the SA node to the AV node and into the ventricles. Efforts to alleviate these problems in the past have included significant usage of various drugs. In some circumstances drug therapy is ineffective and frequently is plagued with side effects such as dizziness, nausea, vision problems, and other difficulties.

An increasingly common medical procedure for the treatment of certain types of cardiac arrhythmia and atrial arrhythmia involves the ablation of tissue in the heart to cut off the path for stray or improper electrical signals. Such procedures are performed many times with an ablation catheter. Typically, the ablation catheter is inserted in an artery or vein in the leg, neck, or arm of the patient and threaded, sometimes with the aid of a guidewire or introducer, through the vessels until a distal tip of the ablation catheter reaches the desired location for the ablation procedure in the heart. The ablation catheters commonly used to perform these ablation procedures produce lesions and electrically isolate or render the tissue non-contractile at particular points in the cardiac tissue by physical contact of the cardiac tissue with an electrode of the ablation catheter and application of energy. The lesion partially or completely blocks the stray electrical signals to lessen or eliminate arrhythmia.

One difficulty in obtaining an adequate ablation lesion using conventional ablation catheters is the constant movement of the heart, especially when there is an erratic or irregular heart beat. Another difficulty in obtaining an adequate ablation lesion is caused by the inability of conventional catheters to obtain and retain uniform contact with the cardiac tissue across the entire length of the ablation electrode surface. Without such continuous and uniform contact, any ablation lesions formed may not be adequate.

It is well known that benefits may be gained by forming lesions in tissue if the depth and location of the lesions being formed can be controlled. In particular, it can be desirable to elevate tissue temperature to around 50° C. until lesions are formed via coagulation necrosis, which changes the electrical properties of the tissue. For example, when sufficiently deep lesions are formed at specific locations in cardiac tissue via coagulation necrosis, undesirable ventricular tachycardias and atrial flutter may be lessened or eliminated. "Sufficiently deep" lesions means transmural lesions in some cardiac applications.

Current techniques for creating continuous linear lesions in endocardial applications include, for example, dragging a conventional catheter on the tissue, using an array electrode, or using pre-formed electrodes. Ablation catheters are not presently designed to be translated within the atria while ablating to form linear lesions. Present catheter designs either require significant technical skill on the part of the surgeon in guiding and placing the catheter by sensitive steering mechanisms. Because of the technical difficulty of operating catheters with such steering mechanisms, ablation procedures can be very time consuming, sometimes taking over three hours or more. Such an extended length of time can exacerbate patient discomfort, both physically and emotionally. In addition, x-ray fluoroscopy is often used throughout the procedure to locate the distal end of the catheter to ensure that it is in the proper location. Clinicians are therefore exposed to significant amounts of radiation on a regular basis because of the lengthy time required for these procedures with present technology.

A particular difficulty encountered with existing ablation catheters is assurance of adequate tissue contact. All of these devices comprise rigid electrodes that do not always conform to the tissue surface, especially when sharp gradients and undulations are present, such as at the ostium of the pulmonary vein in the left atrium and the isthmus of the right atrium between the inferior vena cava and the tricuspid valve. Consequently, continuous linear lesions are difficult to achieve. With present rigid catheters of uniform construction, it can be quite difficult to maintain sufficient contact pressure until an adequate lesion has been formed. This problem is exacerbated on contoured or trabecular surfaces. If the contact between the electrode and the tissue cannot be properly maintained, a quality lesion is unlikely to be formed.

Thus, there remains a need for an ablation instrument that addresses these issues with the existing designs and that permits the formation of uniform spot and continuous linear lesions, including transmural lesions, on smooth or contoured surfaces, and that provides an ease of use not found in previous designs.

The information included in this background section of the specification, including any references cited herein and any description or discussion thereof, is included for technical reference purposes only and is not to be regarded subject matter by which the scope of the invention is to be bound.

BRIEF SUMMARY OF THE INVENTION

The present invention is an ablation catheter that is relatively simple to operate and that provides improved linear lesions. One portion of the catheter acts as a suspension system for the distal tip from which an ablation electrode extends. The suspension system is generally a relatively pliant portion of the catheter that supports the distal end, including the electrode. The suspension system acts as an armature, similar to the armature of a phonograph holding the needle, allowing the electrode to follow the contours of tissue. The catheter is particularly advantageous for ablating a sloped, trabecular surface of endocardial tissue.

One embodiment of a catheter for ablating a surface of endocardial tissue according to the present invention is composed of a distal section of a first material hardness, a proximal section of a second material hardness, and a suspension section of a third material hardness. The third material hardness is less than each of the first material hardness and the second material hardness. The suspension section proximal and adjacent to the distal section and distal and adjacent to the proximal section. An ablation means is also positioned on the distal section of the catheter.

In another embodiment of the invention, the ablation catheter is formed with a component wall structure of composite construction. The wall structure incorporates a tubular metallic braid and a tubular plastic sleeve concentric with and enveloping the tubular metallic braid. The plastic sleeve has multiple adjacent zones of varying stiffness. An ablation electrode is attached to a distal end of the component wall. The adjacent zones of the plastic sleeve may be formed of respective multiple polymeric materials of varying composition arranged collinearly with respect to each other.

Other features, details, utilities, and advantages of the present invention will be apparent from the following more particular written description of various embodiments of the invention as further illustrated in the accompanying drawings and defined in the appended claims.

DETAILED DESCRIPTION OF THE INVENTION

Several embodiments of an endocardial ablation system 2, including an ablation catheter 4 with an armature-type suspension system, an introducer sheath 6, and an ablation electrode 8, according to the present invention is depicted in the figures. As described further below, the endocardial ablation system 2 of the present invention provides a number of advantages, including, for example, mitigating electrode-tissue contact problems. The suspension system of the ablation catheter 4 facilitates enhanced tissue contact in difficult environments (e.g., during ablation of a contoured or trabecular surface on a beating heart), whether creating a spot lesion or a continuous linear lesion, by facilitating contact of the ablation electrode 8 with surface contours of endocardial tissue. This is particularly useful for treatment of atrial flutter where it is desirable to create a linear lesion along the trabecular slope of the isthmus between the ostium of the inferior vena cava and the tricuspid valve in the right atrium.

Figure 1:
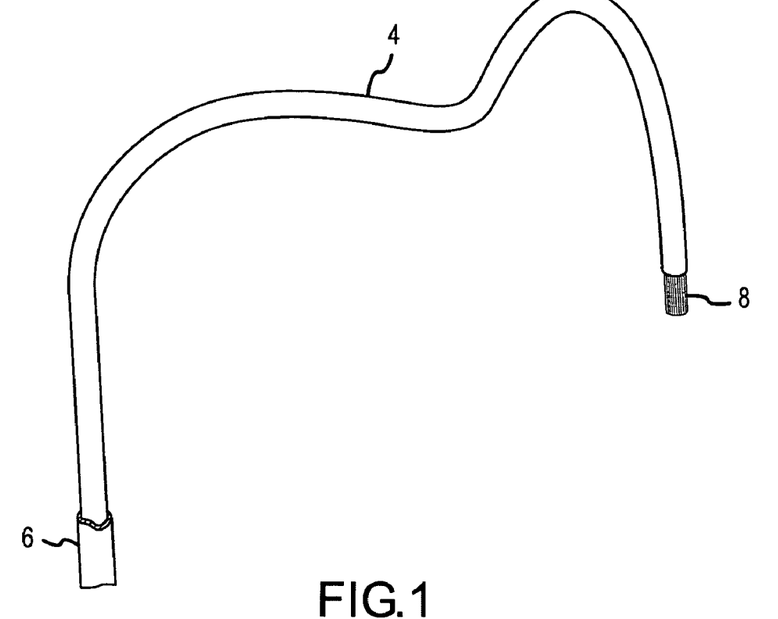
FIG. 1 is an isometric view of an ablation catheter according to one embodiment of the present invention with a sheath substantially cut away.

FIG. 1 is an isometric view of one embodiment of a catheter 4, emerging from a sheath 6 that has been cut away, with an ablation electrode 8 attached to the distal end of the catheter 4. (As used herein, "proximal" refers to a direction away from the body of a patient and toward the clinician. In contrast, "distal" as used herein refers to a direction toward the body of a patient and away from the clinician.) The catheter 4, sheath 6, and ablation electrode 8 together form the endocardial ablation system 2 depicted in detail FIGS. 5-9. The catheter 4 is designed for insertion within a main lumen 10 of the sheath 6 (see FIG. 3). Axiomatically, the diameter of the main lumen 10 is sized to accommodate the outer diameter of the catheter 4.

Figure 2:
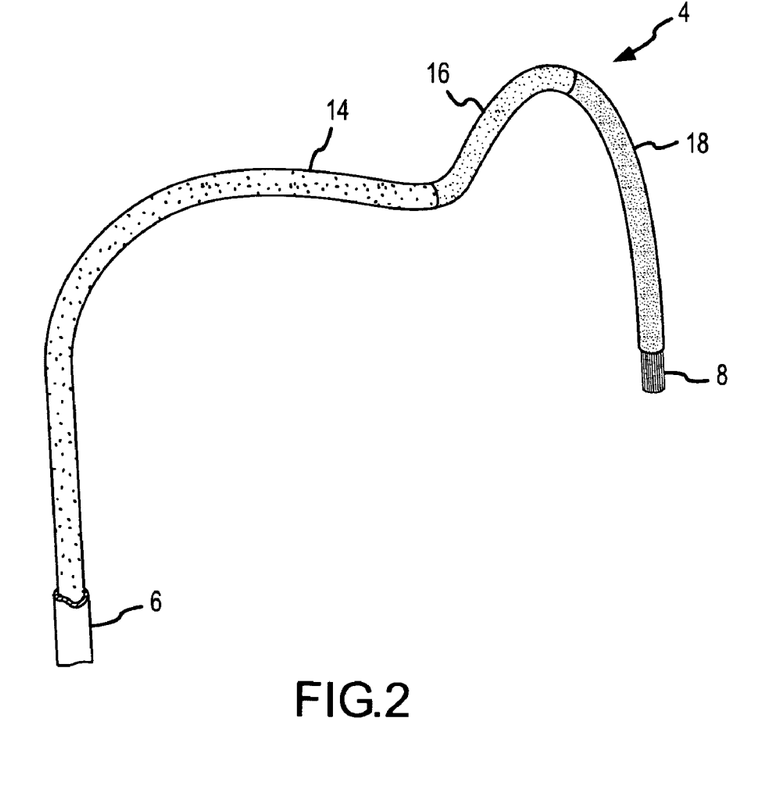
FIG. 2 is an isometric view of the ablation catheter of FIG. 1 detailing several component sections of the catheter.

As shown in FIG. 2, the catheter 4 is a component-built catheter, in this embodiment divided into three sections, a proximal section 14, a suspension section 16, and a distal section 18. The suspension section 16 is located between the proximal section 14 and the distal section 18. In this embodiment, both the proximal section 14 and the distal section 18 are of a more rigid construction than the suspension section 16, which is comparatively pliant. While more rigid than the suspension section 16, the proximal section 14 and the distal section 18 may each have different levels of stiffness or rigidity. In other embodiments it may be desirable to include additional component sections of varying degrees of rigidity depending upon the need of the procedure to be performed. For example, a distal tip of the distal section 18 might be formed of a soft or pliable material to minimize abrasion of the endocardial tissue. If desirable, certain of the component sections may be formed with curved shapes to assist the placement of the catheter 4 based upon the anatomy of the heart. For example, as shown in FIG. 2, the distal section 18 has a slight curve at its proximal end. The suspension section 16 may also have a curve to initiate the orientation of the distal section 18 of the catheter 4 out of the lower port 28. The arc or radius of curvature of a particular section may be selected to allow the catheter 4 to appropriately "fit" in various sizes of heart cavities, to position the catheter 4 with respect to a particular tissue location for ablation application, or to orient the attached ablation electrode 8 at a particular angle or direction. However, each of the sections of the catheter 4 is pliant compared to the sheath 6 and, when introduced into the sheath 6, each of the sections of the catheter 4 is constrained by the sheath 6 and conforms to the orientation of the sheath 6.

Figures 10, 11, 12:
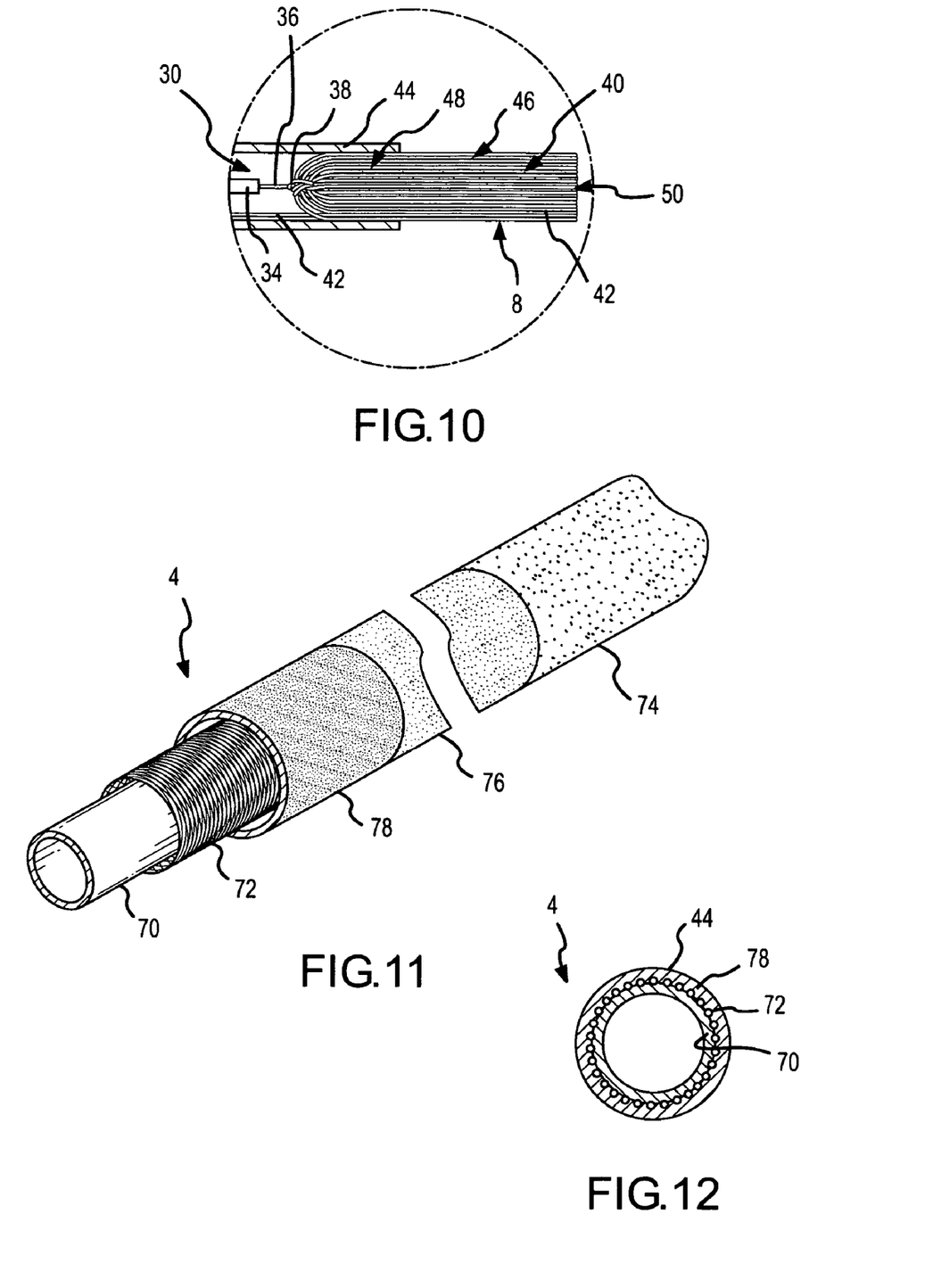
FIG. 10 is an enlarged view of the circled region of FIG. 9 detailing a brush electrode and revealing a conductor making electrical contact with the filaments comprising the brush electrode, and depicting a secondary lead (e.g., for a thermocouple) extending adjacent to the conductor and becoming embedded within the brush filaments.
FIG. 11 is an isometric schematic of the various component materials forming the catheter of the present invention.
FIG. 12 is a cross-section of a catheter formed of the material components of FIG. 11.

As shown in FIG. 2, the catheter 4 may be formed from sections of different materials. FIGS. 11 and 12 depict one exemplary embodiment for forming such a component catheter. The catheter wall 44 may be formed of several layers of materials to ultimately create a composite structure. In the embodiment of FIGS. 11 and 12 the catheter wall is composed of an inner tube 70 of plastic, which is initially surrounded by a cylindrical braid 72 of metal fibers, for example, stainless steel fibers. The metallic braid 72 is included in the catheter wall 44 to add stability to the catheter 4 and also to resist radial forces that might crush the catheter 4. The metallic braid 72 also provides a framework to translate torsional forces imparted by the clinician on the proximal section 14 to the distal end to rotate the catheter 4 for appropriate orientation of the ablation electrode 8. The choice of a flat, angled braid pattern for the metallic braid 72 as depicted adds hoop strength to the catheter 4 without impacting the flexibility of the catheter 4. Based upon the exemplary configuration of FIG. 2, three collinear sections of equal diameter plastic tubing abutted together surround the metallic braid 72. A first tube 74 is composed of a first plastic material, a second tube 76 is composed of a second plastic material, and a third tube 78 is composed of a third plastic material.

The component plastic sections of the catheter wall 44 may be composed, for example, of PEBAX® resins (AUTOFINA Chemicals, Inc., Philadelphia, Pa.), or other polyetherblock co-polyamide polymers, wherein different formulas are used to create the desired material stiffness within each section of the catheter 44. These sections of different material enable the catheter 16 to have, for example, different mechanical properties (e.g., flexibility) at different locations along the catheter shaft. For example, the proximal section 14 of the catheter wall 44 may be formed by the first tube 74 having a relatively stiffer material formulation than the suspension section 16, allowing for greater transfer of control exerted at the proximal end of the catheter 4 to the distal end. The suspension section 16 may be formed by the second tube 76 having a relatively more pliant material formulation than the first tube 74 of the proximal section 14 to provide a level of suspension to the distal tip 18 as further described below. The distal section 18 may be formed by the third tube 78 having a relatively more rigid material formulation to create greater stiffness than the suspension section 16 as well as to provide appropriate support to the ablation electrode 8. The inner tube 70 is generally chosen to have a relatively pliant material formulation. In an exemplary embodiment, the first tube 74 may have a hardness of 72 Shore A, the second tube may have a hardness of 55 Shore A, the third tube may have a hardness of 65 Shore A, and the inner tube may have a hardness of 40 Shore A. The distal section 18 may further be composed of a radiopaque marker to allow a clinician to visualize the position of the tip of the catheter 4 in the heart.

Once the appropriate material qualities of the plastic for each of the inner, first, second, and third tubes 70, 74, 76, 78 are chosen, the catheter wall 44 can be fabricated. As previously described, the inner tube 70 is first surrounded by the metallic braid 72. The first, second, and third tubes 74, 76, 78 are then placed around the metallic braid 72 and are abutted together, end-to-end. The first, second, and third tubes 74, 76, 78 may then be covered by a shrink wrap tube (not shown), if desired, to maintain the close abutment between the adjacent ends of the first, second, and third tubes 74, 76, 78. The layered structure of the inner tube 70, the metallic braid 72, the first, second, and third tubes 74, 76, 78, and the shrink wrap is then heated to a temperature at which the plastic materials composing each of the inner, first, second, and third tubes 70, 74, 76, 78 begins to melt. The plastic of the inner tube 70 flows through the interstices of the metallic braid 72 from the inside. Similarly, the plastic of the first, second, and third tubes 74, 76, 78 flows through the interstices of the metallic braid 72 from the outside. In this manner, the inner tube 70 is welded to the first, second, and third tubes 74, 76, 78 and the metallic braid 72 is encapsulated between them to form the catheter wall 44 as shown in FIG. 12. Similarly, the adjacent ends of the first tube 74 and second tube 76 are welded together and the adjacent ends of the second tube 76 and the third tube 78 are welded together. If the shrink wrap tube is used, it encapsulates the entire catheter wall 44 of the component catheter 4. As indicated above, the various sections of the catheter 4 may be provided with preset curves. Such curvature can be imparted to the catheter 4, for example, by placing a mandrel of a desired form in the catheter 4 and thermally setting the desired curvature to the catheter wall 44. Although the catheter wall 44 depicted in the figures (and as shown in cross-section in FIG. 12) has a circular cross section, the cross-section of the catheter wall 44 may be other than circular.

Figure 3:
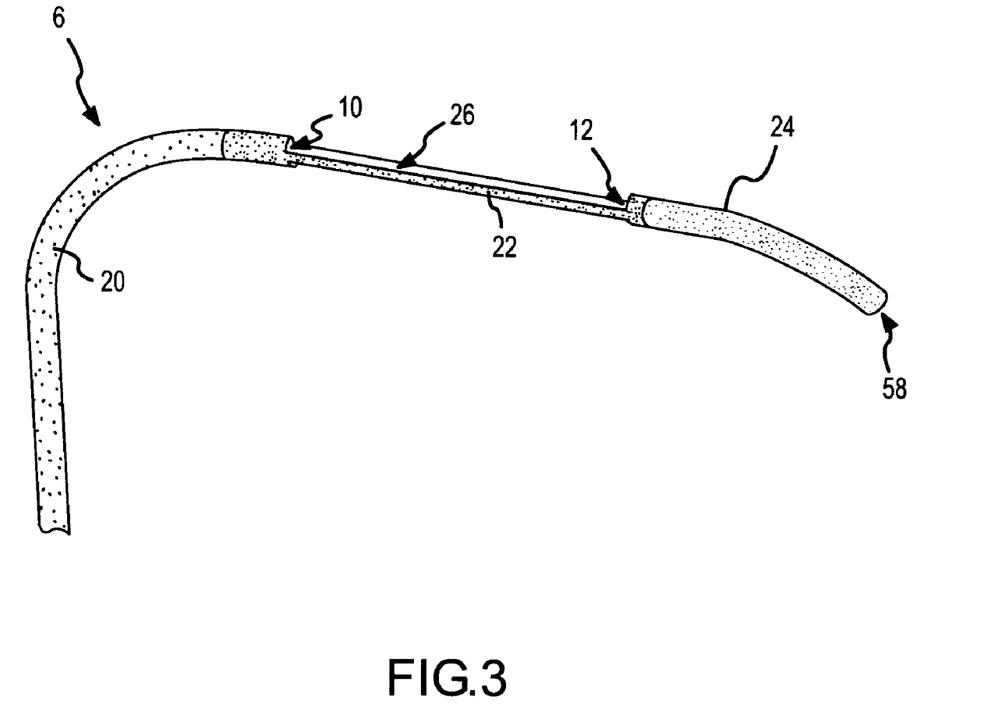
FIG. 3 is a top isometric view of an introducer sheath for use with the ablation catheter of FIG. 1 detailing several component sections of the sheath.
Figure 4:
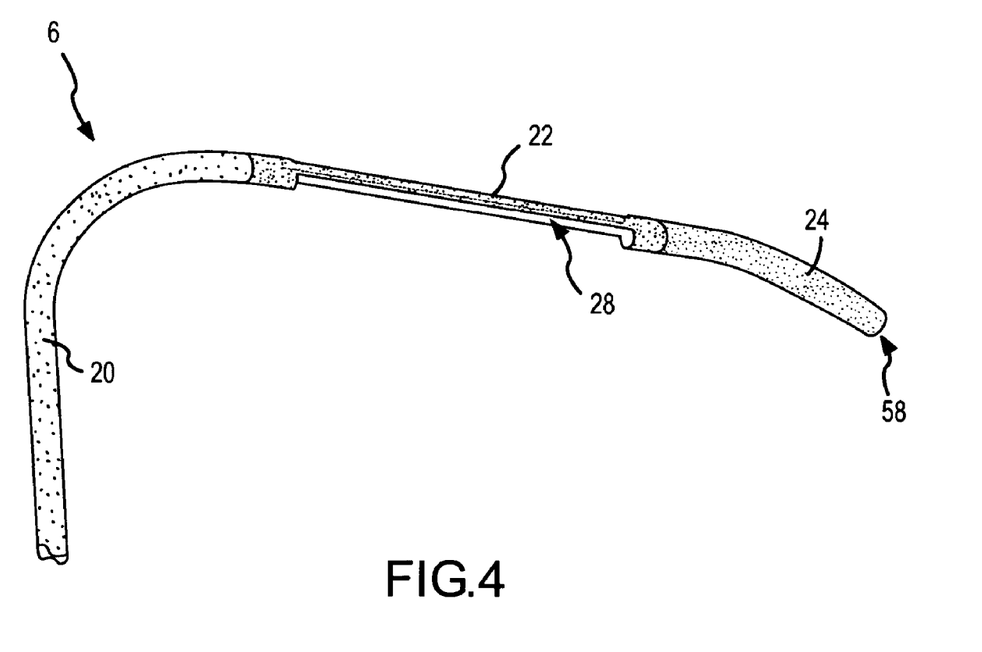
FIG. 4 is a bottom isometric view of the introducer sheath of FIG. 3 detailing several component sections of the sheath.

The introducer sheath 6 may similarly be composed of several component sections of different materials as indicated in FIGS. 3 and 4. A proximal portion 20 of the sheath 6 is connected with a spanning member 22, which is in turn connected with an anchor member 24, which forms the distal end of the sheath 6. Similar to the catheter 4, the proximal portion 20 and the anchor member 24 may be composed, for example, of PEBAX® (poly-ether block amide) resins. In this application, the hardness of the plastic formulations may be greater than that of the catheter 4 in order to guide the catheter 4 within the main lumen 10 and anchor lumen 12 of the sheath 6. The proximal portion 20 and the anchor member 24 may be of the same or different material formulations with similar or different hardness measurements depending upon the needs of the particular procedure to be performed.

The spanning member 22 may be composed of a stiffer material than both the proximal portion 20 and the anchor member 24 of the sheath 6 in order to maintain the integrity of the sheath 6. Two opposing linear slots are formed in the wall of the spanning section 22 of the sheath 6 to create the upper port 26 and the lower port 28. In one exemplary embodiment, these linear slots may each be about 3 cm in length. The formation of such linear slots in the sheath 6 weakens the wall of the sheath 6 because of the significant amount of material removed from the spanning member 22. In order to provide adequate strength, the spanning member 22 may be composed, for example, of a stainless steel tube covered with an aseptic plastic, with an arc-shaped length of material removed on opposite sides of the tube. These arc shaped lengths form the upper port 26 and the lower port 28, respectively, which are defined along the length by thin rectangular walls of remaining material. In alternate embodiments, the upper port 26 may be longer that the lower port 28 or vice versa. The proximal and distal ends of these rectangular walls are integral with tubular caps, which are attached to the proximal portion 20 of the sheath 6 on the proximal end and the anchor member 24 on the distal end. The increased structural rigidity of the spanning member 22 facilitates the stability of the sheath 6 to act as a platform for deployment of the catheter 4 from the upper port 26 and lower port 28.

In an alternate embodiment, the spanning member 22 may be formed of a shape-memory metal in order to provide sufficient tensile strength and alternately flexibility to negotiate the vasculature to reach the heart and enter an atrial chamber. For example, NiTinol, a nickel-titanium (NiTi) alloy with shape-memory properties may be used for the spanning member 22. Shape-memory metals, such as NiTinol are materials that have been plastically deformed to a desired shape before use. Then upon heat application, either from the body as the catheter is inserted into the vasculature or from external sources, the fixation element is caused to assume its original shape before being plastically deformed. NiTinol and other shape-memory alloys are able to undergo a "martensitic" phase transformation that enables them to switch from a "temporary" shape to a "parent" shape at temperatures above a transition temperature. Below that temperature, the alloy can be bent into various shapes. Holding a sample in position in a particular parent shape while heating it to a high temperature programs the alloy to remember the parent shape. Upon cooling, the alloy adopts its temporary shape, but when heated again above the transition temperature the alloy automatically reverts to its parent shape. Alternately, or in addition, shape-memory materials may also be super elastic—able to sustain a large deformation at a constant temperature—and when the deforming force is released they return to their original undeformed shape.

Common formulas of NiTinol have transformation temperatures ranging between −100 and +110° C., have great shape-memory strain, are thermally stable, and have excellent corrosion resistance, which make NiTinol exemplary for use in medical devices for insertion into a patient. For example, the spanning section 22 may be designed using NiTinol with a transition temperature around or below room temperature. Before use the sheath 6 is stored in a low-temperature state. By flushing the sheath 6 with chilled saline solution, the NiTinol spanning section 22 can be kept in its deformed state while positioning the sheath 6 at the desire site. When appropriately positioned, the flow of chilled saline solution can be stopped and the sheath 6 warmed by body heat, or warm saline can be substituted to allow the NiTinol to recover its "preprogrammed" shape.

Figure 13:
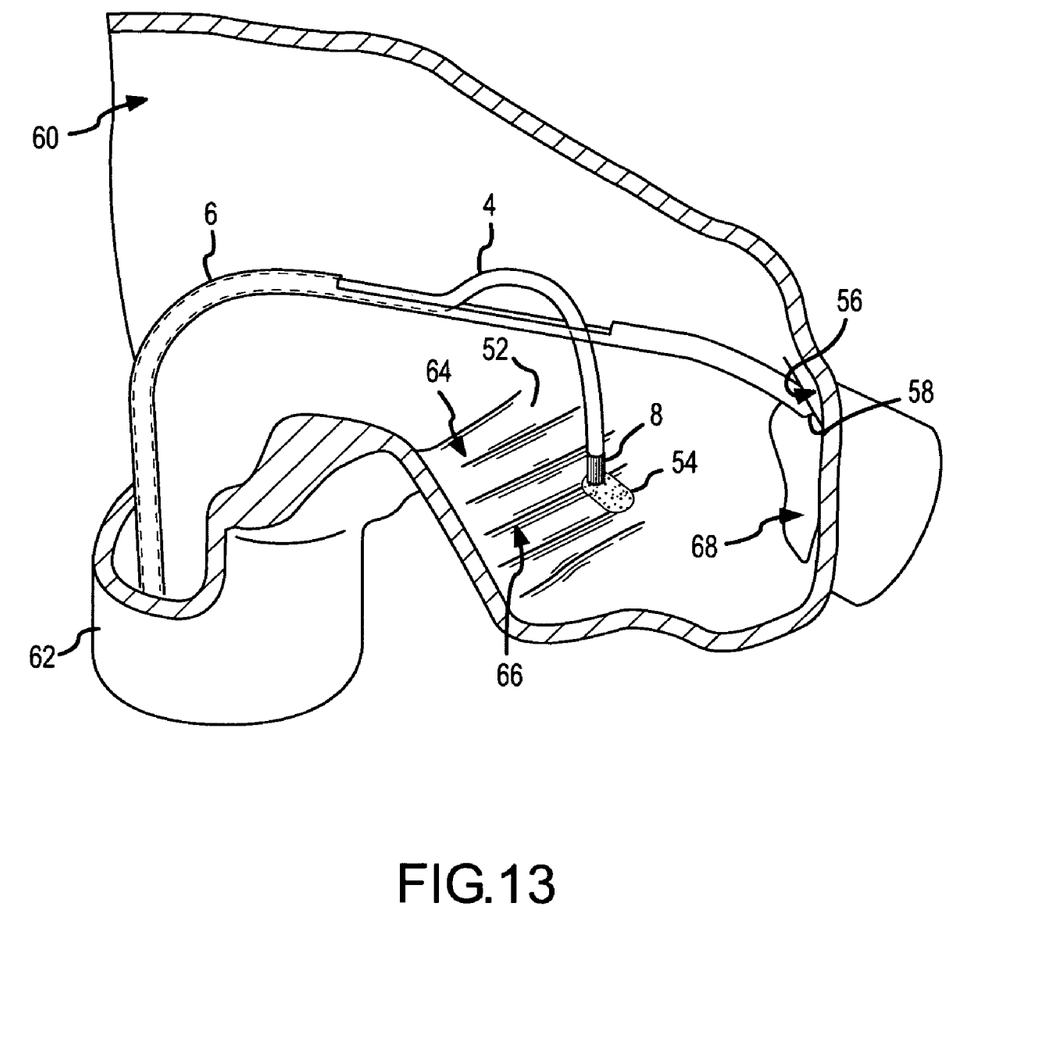
FIGS. 13 and 14 are isometric schematics of the ablation catheter and sheath of FIGS. 1-10 depicting a method of creating a linear lesion in the right atrium.
Figure 14:
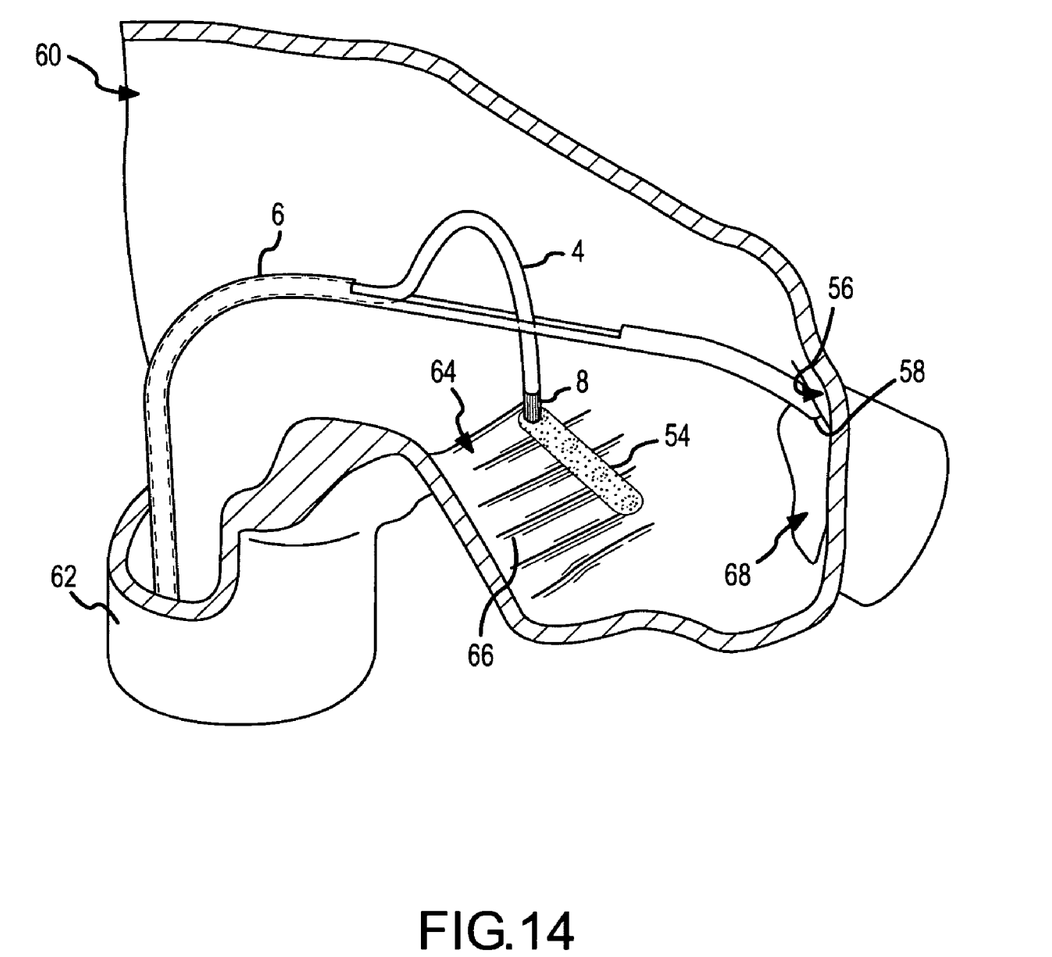
Figure 15:
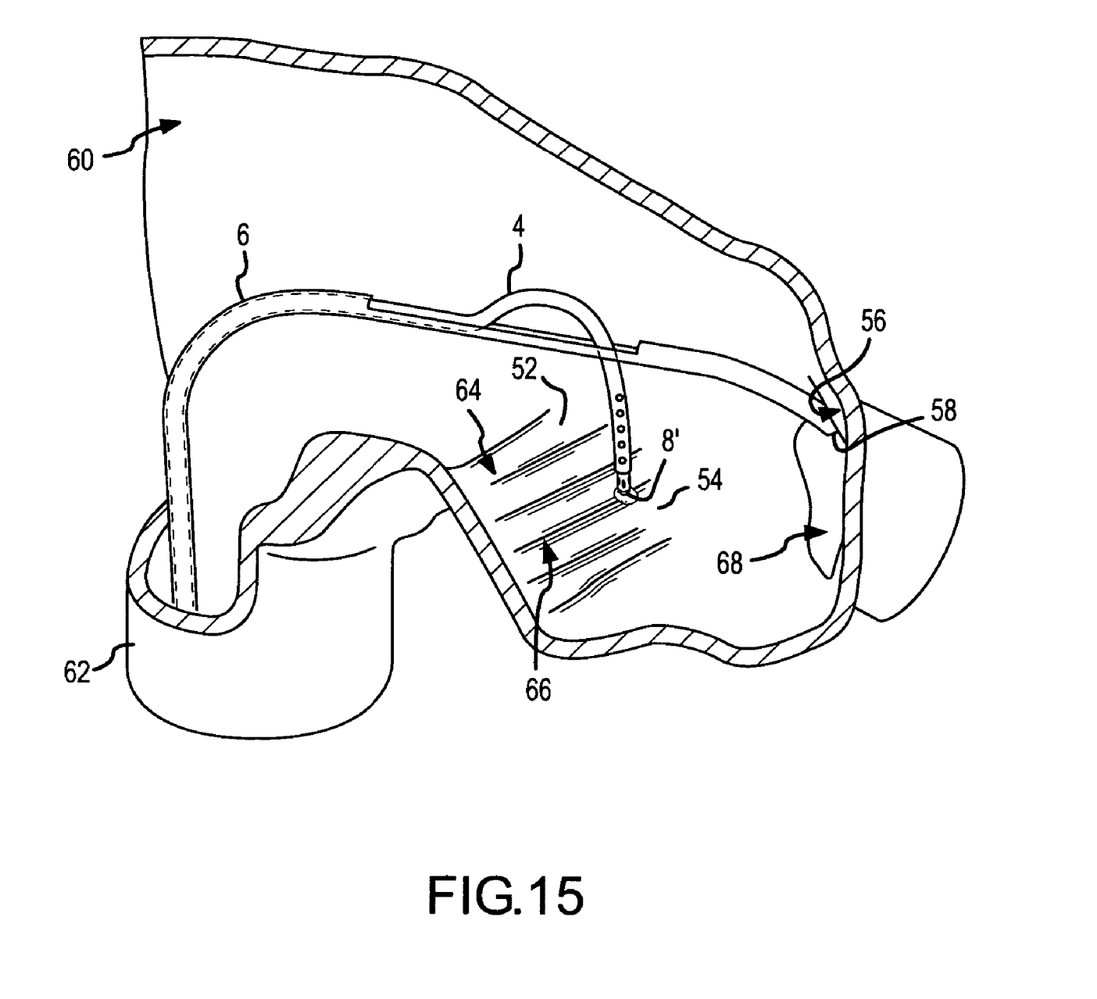
FIG. 15 is an isometric schematic of an alternate embodiment of the ablation catheter of the present invention with a ball electrode depicted in situ in the right atrium.

The anchor member 24 extends distally beyond the spanning member 22. Increased stiffness of the anchor member 24 also helps provide increased structural integrity of the sheath 6. The anchor member 24 may be pressed or anchored against tissue in a cavity of the heart, for example, an atrium wall 56 as shown in FIGS. 13-15, to help stabilize the endocardial ablation system 2 while the heart is beating. The anchor member 24 may be composed of a polymer of greater hardness and/or stiffness than the proximal portion 20 of the sheath 6 or it may even be composed of stainless steel or another suitable material to provide the desired rigidity and structural integrity. The anchor member 24 may terminate with an atraumatic distal tip 58 of a softer material to mitigate possible damage to the atrial wall 56. The distal tip 58 of the anchor member may further have a radiopaque marker to help in identifying the location of the distal end of the sheath 6 during a procedure.

In the particular embodiment of FIGS. 1, 2, and 6-10, a brush electrode 8 is depicted as the ablation electrode 8. A continuous linear lesion 54 (as shown in FIGS. 13-14) is able to be formed because of the superior ability of the filaments 40 of the brush electrode 8 to maintain contact with the tissue 52 and to transfer ablative energy to the tissue 52. In an alternative embodiment, for example, as shown in FIG. 15, the catheter 4 may incorporate a ball electrode 8' as the ablation electrode. Although not as capable of conforming to trabecular surfaces as the brush electrode 8, the ball electrode 8' may be desired for use in certain circumstances for creating spot ablations. Other electrode tips known in the industry may alternately be used if so desired.

The novel brush electrode 8 of the type depicted in FIGS. 1, 2 and 6-10 was originally disclosed in U.S. patent application Ser. No. 10/808,919 filed 24 Mar. 2004, entitled Brush Electrode and Method for Ablation, which is hereby incorporated by reference in its entirety as though fully set forth herein. As shown in greater detail in FIGS. 7-10, the brush electrode 8 may be composed of a plurality of filaments 40, either conductive or nonconductive, arranged in a bundle and protruding from the distal section 18 of the catheter 4. Such a flexible brush electrode 8 provides enhanced tissue contact, particularly for use on contoured or trabecular surfaces.

The filaments 40 may be constructed from a variety of different materials, including nonconductive materials, semi-conductive materials, and conductive materials. For example, the filaments 40 may be formed from metal fibers, metal plated fibers, carbon compound fibers, and other materials. Very thin, carbon fibers may be used. Relatively thicker but less conductive Thunderon® acrylic fibers (Nihon Sanmo Dyeing Company Ltd., Kyoto, Japan) may also be used for the brush electrode filaments 40. Nylon fibers coated with conductive material may also be used. Filaments 40 constructed from metal plated fibers, like coated nylon fibers, may comprise flattened areas around their outer surfaces, resulting in the filaments 40 having noncircular cross-sectional shapes. The brush filaments 40 may be insulated from each other, or they may be in electrical contact with each other. Conductive or nonconductive fluids may flow interstitially between and among the filaments 40 themselves or along the outer surface of the filaments 40.

An embedded portion 48 of the filaments 40 forming the brush electrode 8 may be contained within the catheter lumen 30 at the distal tip 18 of the catheter 4 while an exposed portion 46 may extend distally from the distal tip 18. The exposed portion 46 of the brush electrode 8 may project a few millimeters from the distal tip 18 of the catheter 4. The distance that the exposed portion 46 of the brush electrode 8 extends from the distal tip 18 of the catheter 4 varies depending upon a number of factors including the composition of the filaments 40 comprising the brush electrode 8 and the particular area to be treated with the brush electrode 8. The distal tip 18 of the catheter 4 may itself be conductive or nonconductive.

Figure 5:
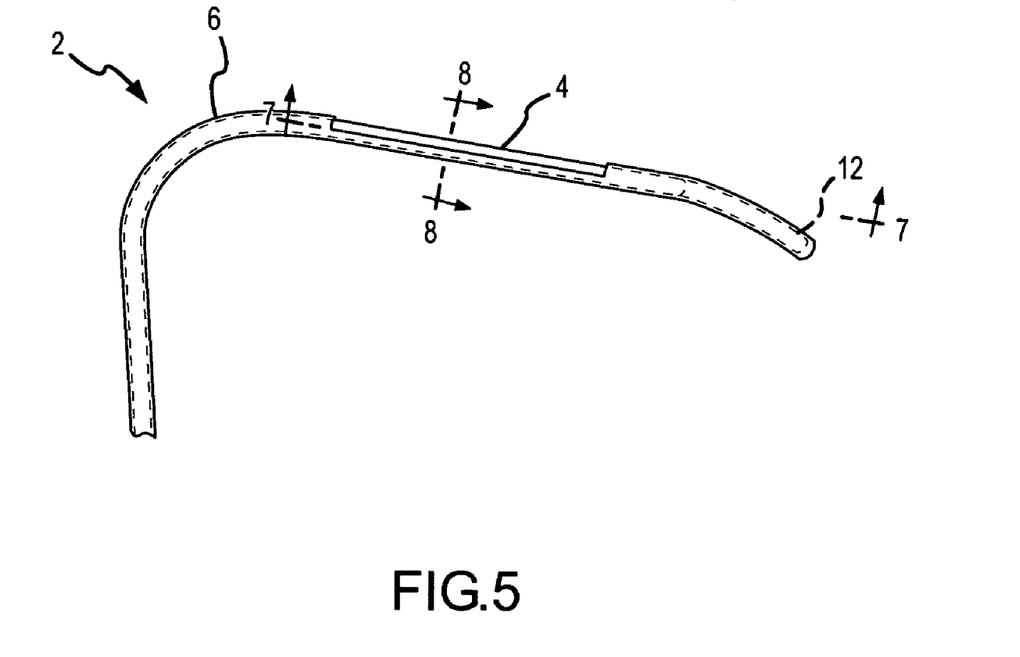
FIG. 5 is an isometric view of the catheter of FIG. 1 carried within the sheath of FIG. 3.
Figure 6:
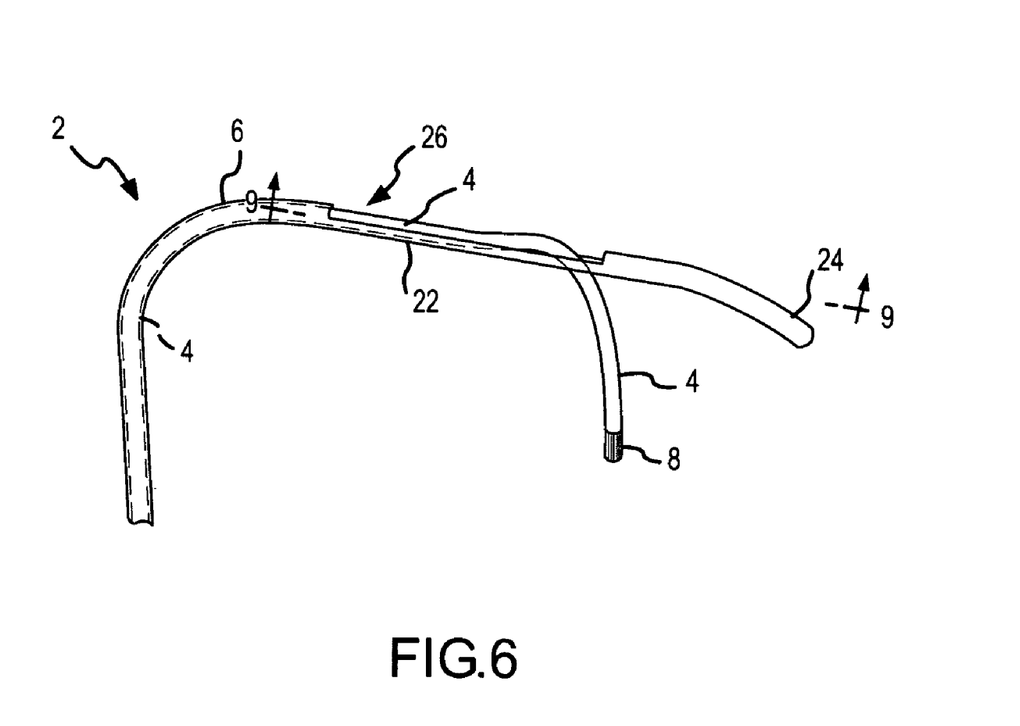
FIG. 6 is an isometric view of the catheter of FIG. 1 unfurling from within the sheath of FIG. 3.
Figure 7:
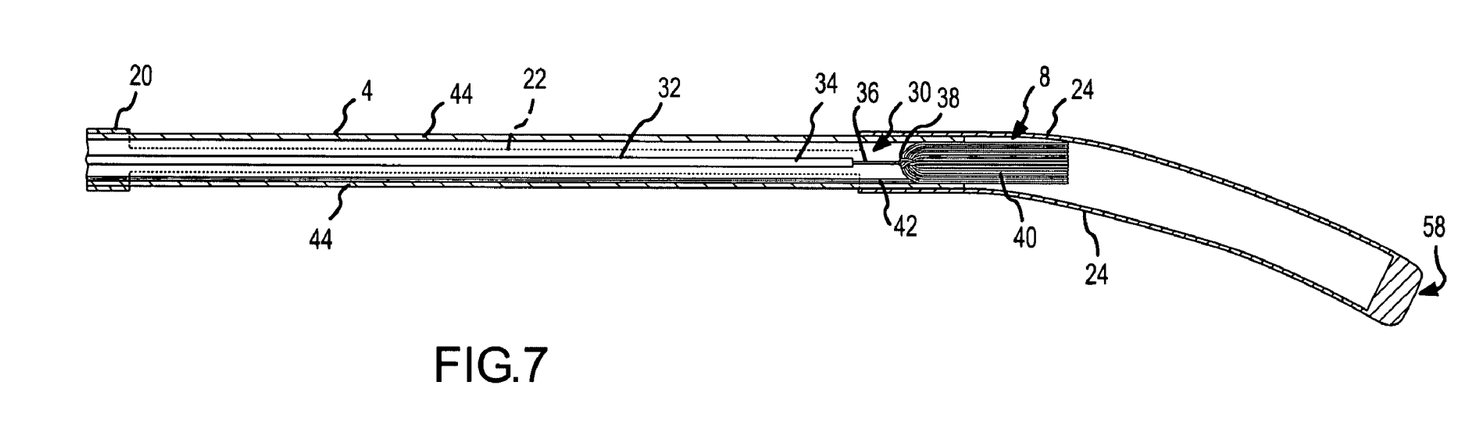
FIG. 7 is a cross-section view, taken along line 7-7 of FIG. 5, of the catheter ablation electrode carried within the sheath.
Figure 9:
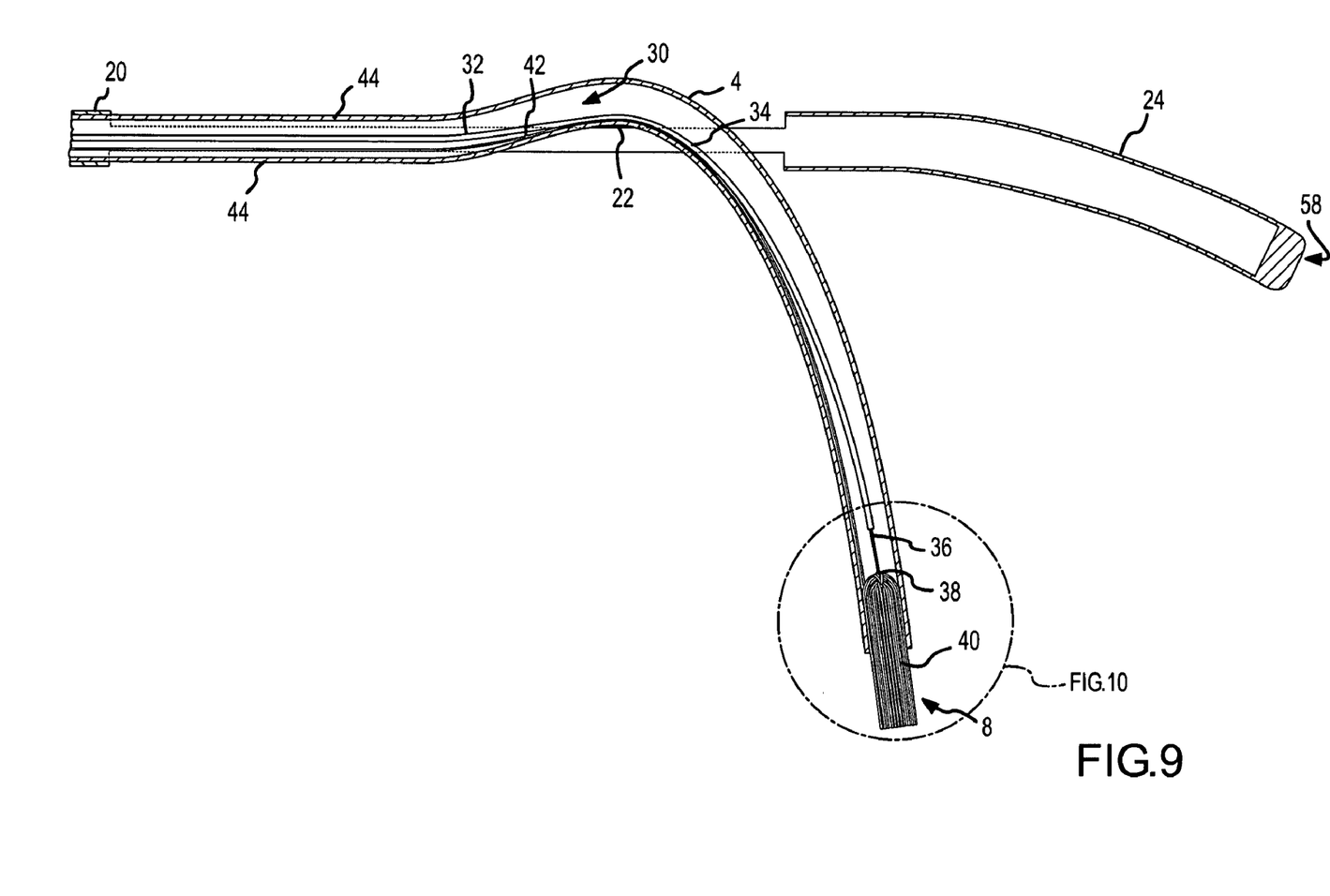
FIG. 9 is a cross-section view, taken along line 9-9 of FIG. 6, of the catheter and ablation electrode unfurling from within the sheath.

FIG. 7 is a cross-section view of the ablation system 2 as shown in FIG. 5 with the catheter 4 and the brush electrode 8 contained within the main lumen 10 and anchor lumen 12 of the sheath 6. FIG. 9 is similarly a cross-section view of the ablation system 2 as shown in FIG. 6, in this instance with the catheter 4 and the brush electrode 8 unfurling from the lower port 28 and upper port 26 of the sheath 6. As depicted in FIGS. 7 and 9, the catheter houses a conductor 32 having an insulated portion 34 and an uninsulated portion 36 that carries ablative energy (e.g., radio frequency current) from an energy source in a controller (not shown) to the brush electrode 8. The conductor 32 extends within the catheter lumen 30 along a longitudinal axis of the catheter 4. The conductor 32 may comprise, for example, insulated copper wire with an uninsulated portion 36 in electrical contact with the brush electrode 8.

Figure 8:
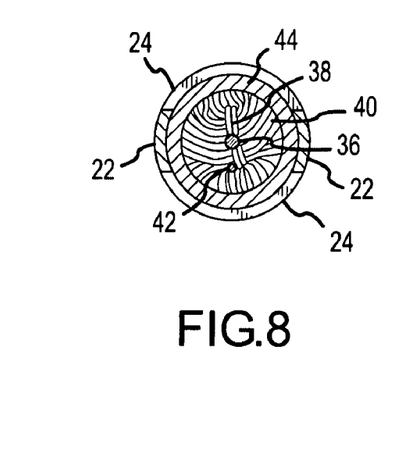
FIG. 8 is a cross-section view, taken along line 8-8 of FIG. 5, of the catheter and ablation electrode within the sheath.

In this embodiment, the uninsulated portion 36 of the conductor 32 is formed or tied in a loop or noose 38 around the embedded portion 48 of the filaments 40 of the brush electrode 8, as shown to better advantage in FIGS. 8 and 10. At the loop or noose 38, ablative energy is transferred from the conductor 32 to the conductive filaments 40 of the brush electrode 8. In this embodiment, the uninsulated portion 36 of the conductor 32 is connected to the embedded portion 48 of the brush electrode 8 so that the connection between the conductor 32 and the brush electrode 8 is protected within the catheter wall 44. A lead 42 may extend substantially parallel to the conductor 32. A distal end of the lead 42 is embedded with the filaments 40 comprising the brush electrode 8, as shown in FIGS. 8 and 10. The lead 42, when present, may be operatively connected to a sensor embedded in the brush electrode 8 (e.g., a thermal sensor, an ultrasound sensor, or a pressure sensor).

FIG. 10 is an enlarged view of the circled region of FIG. 9. As shown in FIG. 10, the brush electrode 8 may have a relatively flat working surface 50 at the distal end 32 of the brush electrode 8. In other words, in this depicted embodiment, all of the filaments 40 comprising the brush electrode 8 extend approximately the same distance from the distal section 18 of the catheter 4. Thus, the brush tip provides a relatively flat working surface 50 comprising the longitudinal ends of the filaments 40. The catheter wall 44 of the distal section 18 of the catheter 4 provides mechanical support for the filaments 40 and may also provide electrical shielding.

The filaments 40 may alternatively be trimmed to provide a variety of configurations and shapes for the working surface 30 of the brush electrode 8, which may provide advantages for special applications of the brush electrode 8. For example, a blade-shape may be formed by creating an edge of longer filaments of the brush electrode 8 resulting in a line of contact with the tissue. Alternatively, the brush electrode 8 may have a wedge-shaped working surface 50 to facilitate angular placement and increase the area of the working surface 50. This configuration may be advantageous for point applications of ablative energy. As another example, the working surface 50 of the brush electrode 8 may have a concave portion or channel, which may be beneficial for wrap-around applications and provide advantages when ablating curved surfaces like the outer surface of a blood vessel. Alternatively, the working surface 50 of the brush electrode 8 may have a convex, trough-shaped tip, which may be beneficial, for example, when reaching into troughs or depressions on a contoured surface. The working surface 50 of the brush electrode 8 may also be domed, hemispherical, a frustum, or conical, coming nearly to a point at the most distal end of the brush electrode 8, with its longest filaments 40 proximal to the longitudinal axis of the catheter 4. The brush electrode 8 is depicted in many of the drawings with a circular cross section, but it may have different cross-sectional configurations.

In one embodiment, conductive or nonconductive fluid may flow through the catheter lumen 30 from a fluid source (e.g., a pump and reservoir in a controller) to the brush electrode 8. When the fluid flows through the brush electrode 8, it creates a wet-brush electrode in which impinging jets of fluid traveling interstitially impact the tissue 52 at an interface between the tissue 52 and the brush electrode 8 to help control temperature changes at the interface. When using conductive fluid and either conductive or nonconductive filaments 40, the brush electrode 8 may act as a virtual electrode. If there is no direct contact between conductive filaments and the tissue 52, or the filaments 40 are entirely nonconductive, the conductive fluid flowing through the catheter lumen 30 makes the electrical contact at the interface between the brush electrode 8 and the tissue 52.

The brush electrode 8 according to the present invention delivers ablative energy to the tissue via the conductive filaments 40 alone, via the conductive fluid alone, or via both the conductive filaments 40 and the conductive fluid. In the latter two configurations, the brush electrode 8 is referred to as a wet-brush electrode. Since it is possible for the conductive fluid to escape from the exposed portion of the wet-brush electrode before reaching the working surface 50 at the distal tip of the wet-brush electrode, there is some ablative energy leakage to the surrounding blood. The leakage of ablative energy to the surrounding blood is in part due to direct contact between the blood and the conductive filaments and in part due to the conductive fluid escaping between the filaments 40 to the surrounding blood, particularly when substantial splaying of the filaments 40 occurs.

As the catheter 4 is further deployed from the sheath 6, the curved section 16 continues to furl and also translates linearly in the direction of the anchor member 58 as indicated by comparison of the positions of the catheter 4 in each of FIGS. 9-11. The deployment of the catheter 4 maintains the distal tip 18 and the attached ablation electrode 8 in contact with the trabecular slope 26 of the isthmus 24.

The creation of a linear lesion 54 in the tissue 52 of the isthmus 64 of the right atrium 60 is depicted schematically in FIGS. 13 and 14. In this procedure, a linear series of ablation lesions is created from the annulus of the tricuspid valve 28 to the inferior vena cava 22 in the isthmus 24 of the right atrial tissue 52 bordering the Eustachian ridge. This isthmus 24 of tissue is critical to the large right atrial reentrant circuit responsible for atrial flutter. The ablation lesions 54 damage atrial tissue 52 preventing the conduction of electrical impulses through the critical isthmus 24. When the line of conduction block is complete, the atrial flutter circuit is shorted and the arrhythmia is cured.

As shown in FIG. 13, the sheath 6 is positioned as desired in the heart, for example, in the right atrium 60 with the distal tip 58 of the anchor member 24 set securely against the atrial wall 56. This placement of the sheath 6 fixes the position of the ablation system 2 and minimizes movement of the ablation system 2 with respect to the heart when the heart beats. A linear lesion 54 is initiated by the deployment of the catheter 4 from the lower port 62 of the sheath 6. When moved proximally out of the anchor lumen 12 such that the ablation electrode 8 is between the spanning members 22, the distal section 18 of the catheter 4 drops from the lower port 38 as the suspension section 16 is not rigid enough to support the distal section 18. In addition, as described above, the suspension section 16 may also be formed with a preset curvature that directs the distal section out of the sheath 6 through the lower port 28. The suspension section 14 bends to create a curved or angled relationship between the proximal section 14 and the distal section 18.

As the distal section 18 drops out of the lower port 28 of the sheath 6, the ablation electrode 8 is oriented toward the sloped isthmus 24 and is placed in contact with the tissue 52, initially on the isthmus 64 adjacent the tricuspid valve 68. Once the ablation electrode contacts the tissue 52, the catheter 4 may further be pushed distally to orient the distal section 18 generally orthogonally to the tissue 52. In order to achieve this orthogonal orientation, the suspension section 16 and the proximal end of the distal section 18 may push through the upper port 26 in the sheath 6. Because the suspension section 16 is of a relatively pliable construction, the suspension section 16 is able to bend easily to allow the distal section 18 to orient appropriately. By creating an orthogonal orientation, a greater surface area of the working surface 50 of the ablation electrode 8 is placed in contact with the tissue 52. Upon activation of a source of ablative energy connected with the ablation electrode 8, the tissue 52 is necrotized and a lesion 54 is formed. As the catheter 4 is further manipulated.

To create a linear lesion along the isthmus 64 of the right atrium 60, the catheter 4 is further manipulated in a similar manner to both relocate the ablation electrode 8 along trabecular surface 36 of the isthmus 2 and maintain the orientation of the distal section 18 generally orthogonal to the tissue 52. From the initial position the catheter 4 may be pulled proximally through the main lumen 10. This movement relaxes the distal section 18 from the orthogonal position and increases the angle formed by the suspension section 16 between the proximal section 14 and the distal section 18 to generally "flatten" the catheter 4. In this manner, the distal section 18, and consequently the ablation electrode 8, is pulled along the isthmus 64. Once moved proximally a small amount to reposition the ablation electrode 8, the catheter 4 may then be moved distally within the main lumen 10. The ablation electrode 8 interfaces with the tissue 52 to maintain its new position, thereby forcing the distal section 18 to again be pushed into a position generally orthogonal to the tissue 52. The distal section 18 is able to return to an orthogonal position because of the flexibility of the suspension section 16, which again forms a smaller angle between the proximal section 14 and the distal section 18 of the catheter 4. This orthogonal orientation again increases the surface area contact of the working surface 50 of the ablation electrode 8 with respect to the tissue 52.

As the ablation electrode is moved along the trabecular slope 66 of the isthmus 64, the distance between the sheath 6 and the tissue 52 decreases. However, the sheath 6 does not interfere with the placement of the ablation electrode 8 because the upper port 26 allows the suspension section 16 and the distal section 18 to extend above the sheath 6 as indicated in FIG. 14. The spanning members 22 further aid the positioning of the ablation electrode 8 by restricting lateral movement of the catheter 4 with respect to the sheath 6. The pliability of the suspension section 16 acts as an armature-type suspension, allowing the ablation electrode 8 to easily follow the undulations of a trabecular surface. By maintaining a close interface between the ablation electrode 8 and the endocardial tissue 52 on the isthmus 64 along a linear path as shown in FIGS. 13 and 14, a continuous linear lesion 54 may be created.

In this manner, the endocardial ablation system 2 of the present invention provides a simple mechanism to direct an ablation electrode to treat a sloped trabecular surface 26 along the isthmus 24 between the inferior vena cava 62 and the tricuspid valve 68 in the right atrium 60. The preset curves of the suspension section 16 and the distal section 18 maintain the orientation of the ablation electrode 8 toward the trabecular slope 66. Further, because of the pliability of the suspension section 16, the distal section 18 may be oriented orthogonally to the isthmus 64 at any point along the trabecular slop 66, regardless of the distance between the sheath 6 and the tissue 52 of the isthmus at a particular point. This allows the ablation catheter 8 to contact any portion of the trabecular slope 66 desired. This is achievable by merely introducing the catheter 4 into the right atrium 60 through the sheath 6 and manipulating the catheter 4 proximally and distally. Thus, the endocardial ablation system 2 of the present invention is relatively easy for a clinician to use compared to the extensive training required to manipulate a steerable catheter or other similar device.

Alternatively, the ablation electrode may embody other electrode forms to achieve particular desired results. For example, FIG. 15 depicts an embodiment of the present invention in which a ball electrode 8' is integrated with the distal section 18 of the catheter 4. A catheter 4 according to the present invention incorporating a ball electrode 8' can similarly be manipulated in conjunction with the sheath 6 of the present invention to ablate tissue 52 and create a lesion 54. Different ablation electrodes in addition to the brush electrode 8 and ball electrode 8' including, for example, virtual electrodes, may also be used depending upon the application or ablation effect desired. However, the advantages of the armature-type suspension system of the endocardial ablation system 2 of the present invention for maintaining tissue contact are applicable regardless of the electrode chosen for use.

Although various embodiments of this invention have been described above with a certain degree of particularity, or with reference to one or more individual embodiments, those skilled in the art could make numerous alterations to the disclosed embodiments without departing from the spirit or scope of this invention. It is intended that all matter contained in the above description and shown in the accompanying drawings shall be interpreted as illustrative only of particular embodiments and not limiting. All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the basic elements of the invention as defined in the following claims.

What is claimed is:

1. A catheter for ablating a surface of endocardial tissue of a beating heart, the catheter comprising:
   a distal section of a first material hardness;

an ablation electrode positioned on the distal section of the catheter;

a proximal section of a second material hardness; and a suspension section of a third material hardness, the suspension section proximal and adjacent to the distal section and distal and adjacent to the proximal section, wherein the third material hardness is less than each of the first material hardness and the second material hardness, whereby the suspension section is adapted to act as a suspension arm to facilitate contact between said ablation electrode and the surface of endocardial tissue while said ablation electrode is tracing a linear lesion along the surface, and wherein the ablation electrode comprises a brush tip.

2. The catheter of claim 1, wherein the suspension section further comprises a preset curve for orienting the distal section toward the surface of endocardial tissue.

3. The catheter of claim 1, wherein at least one of the proximal portion, the suspension portion, and the distal portion comprises a preset curve for appropriately orienting the catheter.

4. The catheter of claim 3, wherein the preset curve comprises an inverted U-shaped curve to orient the ablation electrode toward the surface of endocardial tissue.

5. The catheter of claim 1, wherein the first material hardness is greater than the second material hardness.

6. The catheter of claim 1, wherein the first material hardness is less than the second material hardness.

7. The catheter of claim 1, wherein the first material hardness is equal to the second material hardness.

8. The catheter of claim 1, wherein the ablation electrode comprises a distal surface having a shape selected from the group consisting of concave, convex, wedge shaped, domed, hemispherical, conical, and a frustum.

9. An ablation catheter, comprising:

a component wall structure of composite construction incorporating a tubular metallic braid; and a tubular plastic sleeve concentric with and enveloping the tubular metallic braid, the plastic sleeve further comprising multiple adjacent zones of varying stiffness; and an ablation electrode attached to a distal end of the component wall, wherein the ablation electrode comprises a brush tip.

10. The ablation catheter of claim 9, wherein the adjacent zones comprise respective multiple polymeric materials of varying composition arranged collinearly with respect to each other.

11. The ablation catheter of claim 10, wherein the multiple polymeric materials comprise varying compositions of PEBAX (poly-ether block amide).

12. The ablation catheter of claim 10, wherein the respective multiple polymeric materials are welded together end-to-end.

13. The ablation catheter of claim 9, wherein the component wall structure further incorporates an inner plastic tube concentric with and enveloped by the tubular metallic braid.

14. The ablation catheter of claim 13, wherein the inner plastic tube is welded to the outer plastic sleeve whereby the tubular metallic braid is encapsulated between the inner plastic tube and the outer plastic sleeve.

15. The ablation catheter of claim 13, wherein the inner plastic tube is of a uniform stiffness.

16. The ablation catheter of claim 9, wherein at least one zone is sufficiently pliable to act as a suspension for the distal end of the component wall, allowing the ablation electrode to maintain constant contact with tissue while tracing a trabecular tissue surface.

17. A catheter for ablating a surface of endocardial tissue of a beating heart, the catheter comprising:

a distal section of a first material hardness;

an ablation electrode positioned on the distal section of the catheter, said ablation electrode comprising a brush tip;

a proximal section of a second material hardness; and a suspension arm of a third material hardness, the suspension arm being coupled to the proximal section, wherein the third material hardness is less than each of the first material hardness and the second material hardness, whereby the suspension arm is adapted to facilitate contact between said ablation electrode and the surface of endocardial tissue while said ablation electrode is tracing a linear lesion along the surface.

* * * * *